US00PP30443P2

(12) United States Plant Patent
Holtmaat

(10) Patent No.: US PP30,443 P2
(45) Date of Patent: Apr. 23, 2019

(54) ***HEUCHERA* PLANT NAMED 'REX PURPLE'**

(50) Latin Name: ***Heuchera hybrid* X *Heuchera villosa***
Varietal Denomination: Rex Purple

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/732,941

(22) Filed: Jan. 12, 2018

(51) Int. Cl.
*A01H 5/00* (2018.01)

(52) U.S. Cl.
USPC ..... Plt./440

(58) Field of Classification Search
USPC ..... Plt./440
See application file for complete search history.

(56) References Cited

PUBLICATIONS

PLUTO Plant Variety Database Nov. 3, 2018.*

* cited by examiner

*Primary Examiner* — Annette H Para
(74) *Attorney, Agent, or Firm* — C. A. Whealy

(57) ABSTRACT

A new and distinct cultivar of *Heuchera* plant named 'Rex Purple', characterized by its uniformly mounded plant habit; densely foliated and bushy appearance; greyed purple-colored leaves; long flowering period; numerous inflorescences with sterile white and red purple-colored flowers; resistance to Powdery Mildew; and good garden performance.

2 Drawing Sheets

Botanical designation: *Heuchera* hybrid X *Heuchera villosa.*

Cultivar denomination: 'REX PURPLE'.

BACKGROUND OF THE INVENTION

The present invention relates to a new and distinct *Heuchera* plant of *Heuchera*, botanically known as *Heuchera* hybrid X *Heuchera villosa* and hereinafter referred to by the name 'Rex Purple'.

The objective of the breeding program is to create new compact *Heuchera* plants with attractive leaf colors, less sensitivity to Powdery Mildew and good garden performance.

The new *Heuchera* plant originated from a cross-pollination in July, 2014 in Zuidwolde, The Netherlands of *Heuchera* hybrid 'Mars', not patented, as the female, or seed, parent with a proprietary selection of *Heuchera villosa* identified as code number 083-C047, not patented, as the male, or pollen, parent. The new *Heuchera* plant was discovered and selected by the Inventor as a single flowering plant from within the progeny of the stated cross-pollination in a controlled greenhouse environment in Zuidwolde, The Netherlands in June, 2015.

Asexual reproduction of the new *Heuchera* plant by in vitro meristem culture in a controlled environment in Zuidwolde, The Netherlands since March, 2017 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Rex Purple'. These characteristics in combination distinguish 'Rex Purple' as a new and distinct *Heuchera* plant:

1. Uniformly mounded plant habit.
2. Densely foliated and bushy appearance.
3. Greyed purple-colored leaves.
4. Long flowering period.
5. Numerous inflorescences with sterile white and red purple-colored flowers.
6. Resistance to Powdery Mildew.
7. Good garden performance.

Plants of the new *Heuchera* differ from plants of the female parent, 'Mars', in leaf color as plants of 'Mars' have greyed green-colored leaves. In addition, plants of the new *Heuchera* have larger leaves than plants of 'Mars'.

Plants of the new *Heuchera* differ from plants of the male parent selection in leaf color as plants of the male parent selection have more grey-colored leaves. In addition, plants of the new *Heuchera* have smaller leaves than plants of the male parent selection.

Plants of the new *Heuchera* can be compared to plants of *Heuchera* hybrid 'Shanghai', disclosed in U.S. Plant Pat. No. 21,859. In side-by-side comparisons, plants of the new *Heuchera* differ primarily from plants of 'Shanghai' in plant size as plants of the new *Heuchera* are taller than plants of 'Shanghai'. In addition, plants of the new *Heuchera* have larger leaves than plants of 'Shanghai'.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph on the first sheet is a side perspective view of a typical flowering plant of 'Rex Purple' grown in a container.

The photograph at the top of the second sheet is a close-up view of typical inflorescences of 'Rex Purple'.

The photograph at the bottom of the second sheet is a close-up view of typical leaves of 'Rex Purple'.

DETAILED BOTANICAL DESCRIPTION

The aforementioned photographs and following observations, measurements and values describe plants grown during the late spring and early summer in 2-liter containers in an outdoor nursery in Wieringerwerf, The Netherlands and under cultural practices typical of commercial *Heuchera* production. During the production of the plants, day temperatures ranged from 18° C. to 30° C. and night temperatures ranged from 6° C. to 18° C. Plants were one year old when the photographs and the description were taken. In the description, color references are made to The Royal Horticultural Society Colour Chart, 2015 Edition, except where general terms of ordinary dictionary significance are used.

Botanical classification: *Heuchera* hybrid X *Heuchera villosa* 'Rex Purple'.

Parentage:

- *Female, or seed, parent.*—*Heuchera* hybrid 'Mars', not patented.
- *Male, or pollen, parent.*—Proprietary selection of *Heuchera villosa* identified as code number 083-C047, not patented.

Propagation:

- *Type.*—By in vitro meristem culture.
- *Time to initiate roots, summer.*—About 15 days at temperatures about 20° C.
- *Time to produce a rooted young plant, summer.*—About two months at temperatures about 20° C.
- *Root description.*—Medium in thickness, fibrous; typically creamy white in color, actual color of the roots is dependent on substrate composition, water quality, fertilizer type and formulation, substrate temperature and physiological age of roots.
- *Rooting habit.*—Moderately freely branching; medium density.

Plant description:

- *Plant and growth habit.*—Herbaceous perennial; basal rosette plant habit with leaves developing from the base; densely foliated and dense and bushy appearance; mounded plant habit; moderately vigorous growth habit; moderate growth rate.
- *Plant height, soil level to top of foliar plane.*—About 35.7 cm.
- *Plant height, soil level to top of inflorescences.*—About 63.5 cm.
- *Plant diameter or spread.*—About 62.6 cm.

Leaf description:

- *Arrangement.*—Alternate in basal rosettes; simple.
- *Length.*—About 13.4 cm.
- *Width.*—About 12.6 cm.
- *Shape.*—Overall, broad ovate to close to orbicular; palmately lobed.
- *Apex.*—Short and abruptly acute.
- *Base.*—Hastate, lobes moderately to strongly imbricate.
- *Margin.*—Crenate with about nine lobes; sinuses shallow and divergent.
- *Texture and luster, upper surface.*—Densely pubescent; matte.
- *Texture and luster, lower surface.*—Densely pubescent; moderately glossy.
- *Venation pattern.*—Palmate; reticulate.
- *Color.*—Developing leaves, upper surface: Close to 187C; apices, close to N200A. Developing leaves, lower surface: Close to 187B. Fully expanded leaves, upper surface: Close to N187B; venation, close to between 147A and N200A. Fully expanded leaves, lower surface: Close to between N79B and N186D; venation, close to between N79B and N186D.
- *Petioles.*—Length: About 22.8 cm. Diameter: About 4 mm. Strength: Moderately strong. Texture and luster, upper and lower surfaces: Densely pubescent; glossy. Color, upper and lower surfaces: Close to N186C.

Flower description:

- *Flower type and flowering habit.*—Single campanulate flowers arranged on compound spikes; each spike with about 120 flowers; about 3,000 flowers develop per plant during the flowering season; flowers face mostly upright, outward to slightly nodding.
- *Fragrance.*—None detected.
- *Time of flowering.*—Plants flower continuously from the late spring into the autumn in The Netherlands; plants begin flowering about four months after planting.
- *Inflorescence longevity.*—Individual flowers last a few weeks on the plant; flowers not persistent.
- *Inflorescence length.*—About 22.9 cm.
- *Inflorescence width.*—About 7.7 cm.
- *Flower diameter.*—About 7 mm.
- *Flower depth (height).*—About 9 mm.
- *Flower buds.*—Height: About 3.5 mm. Diameter: About 2.5 mm. Shape: Obovate. Texture and luster: Densely pubescent; matte. Color: Close to 62A to 62B; towards the base, close to N77B.
- *Petals.*—Quantity and arrangement: Five petals in a single whorl. Length: About 4.5 mm. Width: About 2 mm. Shape: Oblanceolate. Apex: Acute. Base: Narrowly attenuate. Margin: Entire. Texture and luster, upper and lower surfaces: Smooth, glabrous; matte. Color: When opening, upper and lower surfaces: Close to NN155D. Fully opened, upper and lower surfaces: Close to NN155D; color does not change with development.
- *Sepals.*—Quantity and arrangement: Five sepals in a single whorl; fused at base. Length: About 6 mm. Width: About 3 mm. Shape: Oblong. Apex: Obtuse. Margin: Entire. Texture and luster, upper and lower surfaces: Densely pubescent; matte. Color: When opening, upper and lower surfaces: Close to 62D; towards the base, close to 186C to 186D. Fully opened, upper and lower surfaces: Close to 62D; margins, close to NN155B; towards the base, close to N74C to N74D.
- *Peduncles.*—Length: About 47.7 cm. Diameter: About 3 mm. Strength: Moderately strong. Aspect: About 25° from vertical. Texture and luster: Densely pubescent; moderately glossy Color: Close to between N187C and N200A.

*Pedicels*.—Length: About 3 mm. Diameter: About 0.5 mm. Strength: Moderately strong. Aspect: About 45° from peduncle axis. Texture and luster: Densely pubescent; matte. Color: Close to 148A.

*Reproductive organs*.—Androecium: Stamen number: Five per flower. Filament length: About 4 mm. Filament color: Close to NN155D. Anther length: About 1 mm. Anther shape: Deltoid. Anther color: Close to 20B to 20C. Amount of pollen: Scarce to moderate. Pollen color: Close to 22A. Gynoecium: Pistil number: Two per flower. Pistil length: About 5 mm. Style length: About 4.75 mm. Style color: Close to NN155D; proximally, close to N155B. Stigma diameter: About 0.2 mm. Stigma shape: Club-shaped. Stigma color: Close to N155B. Ovary color: Close to 150D.

*Seeds and fruits*.—Flowers of plants of the new *Heuchera* are sterile. Seed and fruit development have not been observed on plants of the new *Heuchera* to date.

Pathogen & pest resistance: Plants of the new *Heuchera* have been observed to be relatively resistant to Powdery Mildew (*Sphaerotheca macularis*). Resistance to pests and other pathogens has not been observed on plants of the new *Heuchera* grown under commercial conditions to date.

Garden performance: Plants of the new *Heuchera* have been observed to have good garden performance and to tolerate high temperatures about 35° C. and to be suitable for USDA Hardiness Zones 3 through 9.

It is claimed:

1. A new and distinct *Heuchera* plant named 'Rex Purple' as illustrated and described.

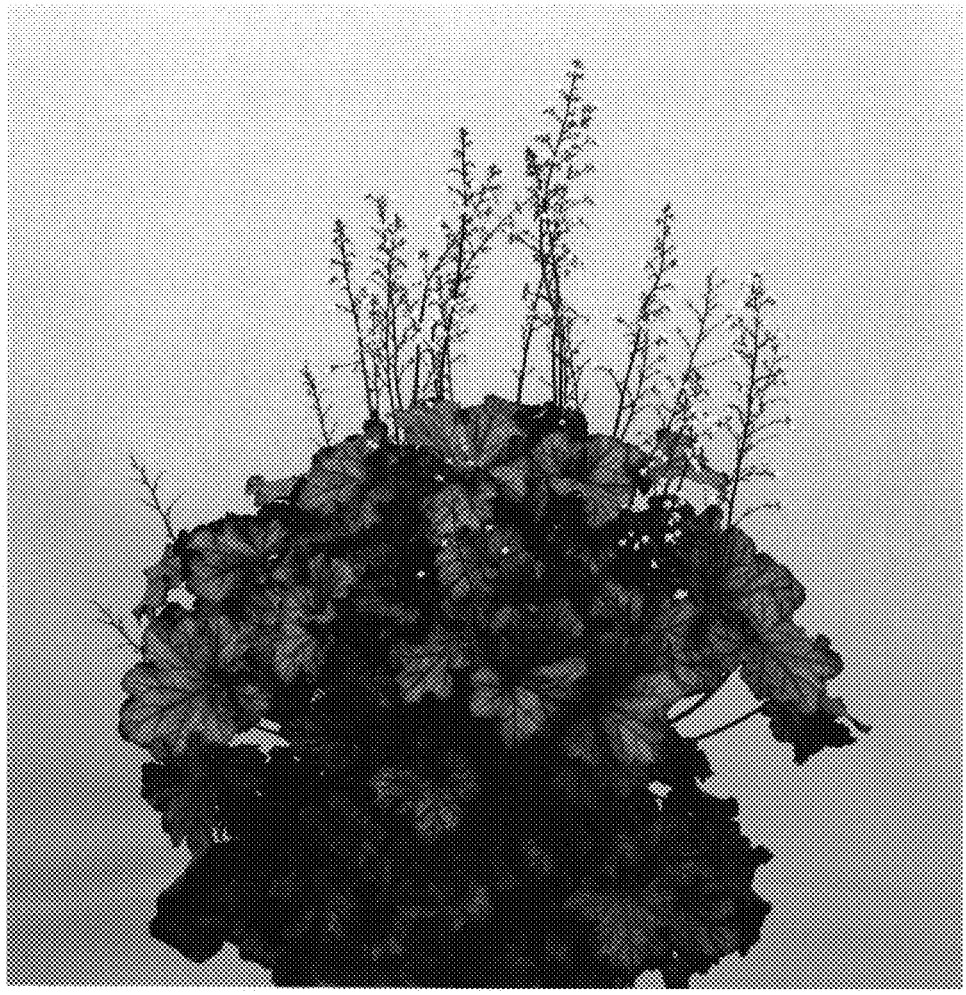

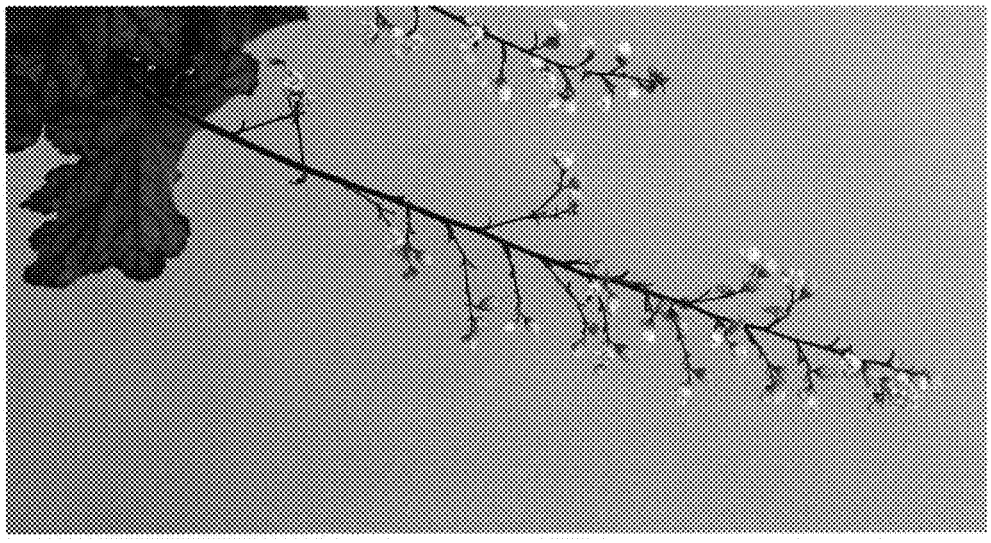
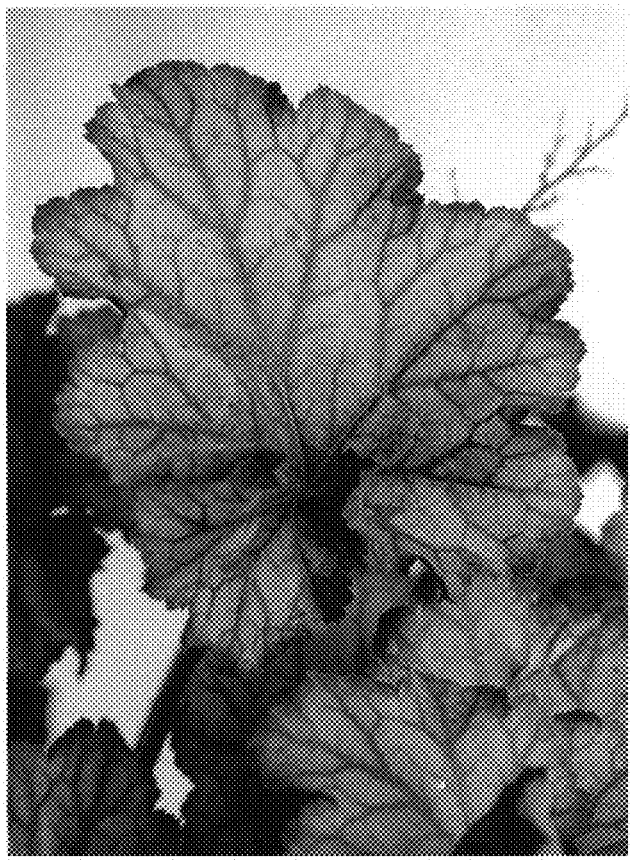

* * * * *